(12) United States Patent
Betancur et al.

(10) Patent No.: US 10,362,976 B2
(45) Date of Patent: Jul. 30, 2019

(54) STERILE FLUID COLLECTION TUBE PACKAGE

(71) Applicant: Boca Dental Supply, LLC, Boca Raton, FL (US)

(72) Inventors: Alvaro Betancur, Boca Raton, FL (US); Paula Betancur, Boca Raton, FL (US)

(73) Assignee: Boca Dental Supply, LLC, Boca Raton, FL (US)

( * ) Notice: Subject to any disclaimer, the term of this patent is extended or adjusted under 35 U.S.C. 154(b) by 482 days.

(21) Appl. No.: 14/992,631

(22) Filed: Jan. 11, 2016

(65) Prior Publication Data

US 2016/0198990 A1    Jul. 14, 2016

Related U.S. Application Data

(60) Provisional application No. 62/102,683, filed on Jan. 13, 2015.

(51) Int. Cl.
| | |
|---|---|
| *B65D 83/10* | (2006.01) |
| *A61B 5/15* | (2006.01) |
| *A61B 50/33* | (2016.01) |
| *A61B 10/00* | (2006.01) |
| *B65D 85/00* | (2006.01) |

(Continued)

(52) U.S. Cl.
CPC .... *A61B 5/150305* (2013.01); *A61B 5/15003* (2013.01); *A61B 5/150351* (2013.01); *A61B 5/150786* (2013.01); *A61B 10/0096* (2013.01); *A61B 50/33* (2016.02); *B01L 9/06* (2013.01); *B65D 75/326* (2013.01); *B65D 75/328* (2013.01); *B65D 85/00* (2013.01); *A61B 2050/002* (2016.02);

(Continued)

(58) Field of Classification Search
CPC .... B65D 75/326; B65D 75/328; B65D 85/00; B65D 2575/3218; A61B 5/150305; A61B 50/33; A61B 5/15003
USPC .......................... 206/363, 370, 438, 471, 571
See application file for complete search history.

(56) References Cited

U.S. PATENT DOCUMENTS

| | | | |
|---|---|---|---|
| 3,270,877 | A | 9/1966 | Hecker |
| 3,272,371 | A | 9/1966 | Weiner |

(Continued)

FOREIGN PATENT DOCUMENTS

| | | |
|---|---|---|
| CN | 201411157 Y | 2/2010 |
| FR | 2745264 A1 | 8/1997 |

OTHER PUBLICATIONS

"International Search Report and Written Opinion of the International Searching Authority for PCT Application No. PCT/US16/12915", dated Mar. 17, 2016, 9 Pages.

(Continued)

*Primary Examiner* — Luan K Bui
(74) *Attorney, Agent, or Firm* — Medley, Behrens & Lewis, LLC

(57) ABSTRACT

Various technologies presented herein relate to sterile transport, storage and operation of fluid collection tubes. A plurality of sterile sample tube packages are presented, wherein each package comprises a tray (having a recessed cavity formed therein), one or more fluid collection tubes and a cover. Each cavity includes at least one compartment, wherein a collection tube can be respectively stored in each compartment. The tray and cover can be formed from medically sterile materials.

17 Claims, 4 Drawing Sheets

(51) Int. Cl.
　　*B01L 9/06*　　　(2006.01)
　　*B65D 75/32*　　(2006.01)
　　*A61B 50/00*　　(2016.01)
(52) U.S. Cl.
　　CPC . *A61B 2050/0065* (2016.02); *B01L 2200/141* (2013.01); *B65D 2575/3218* (2013.01)

(56) References Cited

U.S. PATENT DOCUMENTS

| | | | |
|---|---|---|---|
| 3,589,511 A | 6/1971 | Britt | |
| 3,676,159 A * | 7/1972 | Fallowfield | B65D 1/36 206/205 |
| 3,869,043 A * | 3/1975 | Warner | B65D 75/36 206/385 |
| 4,324,331 A * | 4/1982 | Ignasiak | A61L 2/26 206/363 |
| 4,572,371 A * | 2/1986 | Asenbauer | B01L 9/06 206/443 |
| 4,890,765 A | 1/1990 | Haber et al. | |
| 5,082,112 A * | 1/1992 | Dunklee | A61B 1/00142 206/363 |
| 5,176,258 A * | 1/1993 | Antal | B65D 75/326 206/438 |
| 5,199,567 A | 4/1993 | Discko, Jr. | |
| 5,246,109 A * | 9/1993 | Markle | A61B 5/145 206/363 |
| 5,261,208 A | 11/1993 | Lockhart | |
| 5,390,792 A * | 2/1995 | Van Ness | A61L 2/26 206/213.1 |
| 5,997,811 A | 12/1999 | Esposito | |
| 8,530,231 B2 | 9/2013 | Nakae et al. | |
| 2008/0135443 A1 * | 6/2008 | Frojd | A61M 5/002 206/571 |
| 2013/0062229 A1 * | 3/2013 | Weissbrod | B65D 25/103 206/223 |

OTHER PUBLICATIONS

"International Preliminary Report on Patentability for PCT Application No. PCT/US16/12915", dated Jul. 27, 2017, 8 Pages.

\* cited by examiner

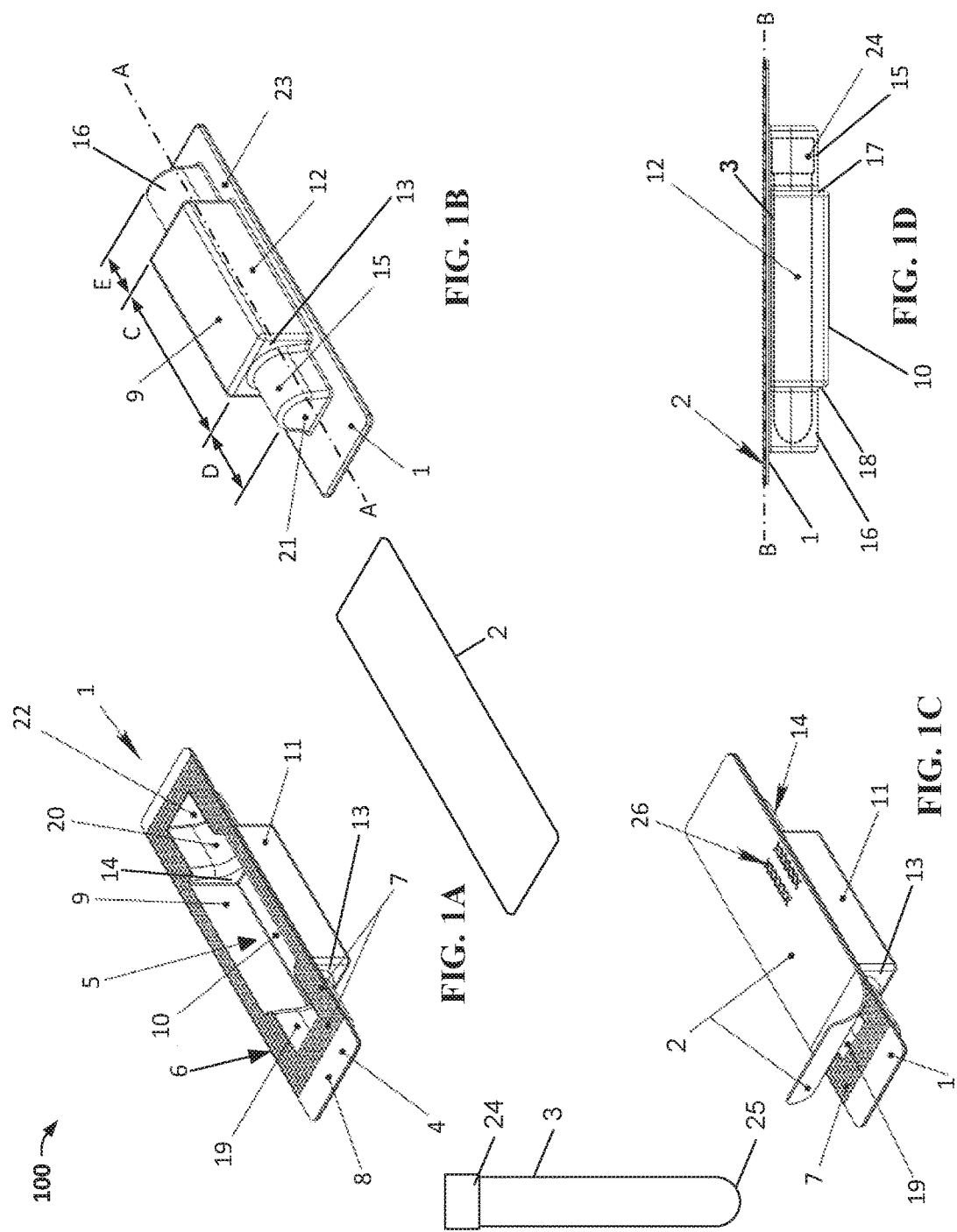

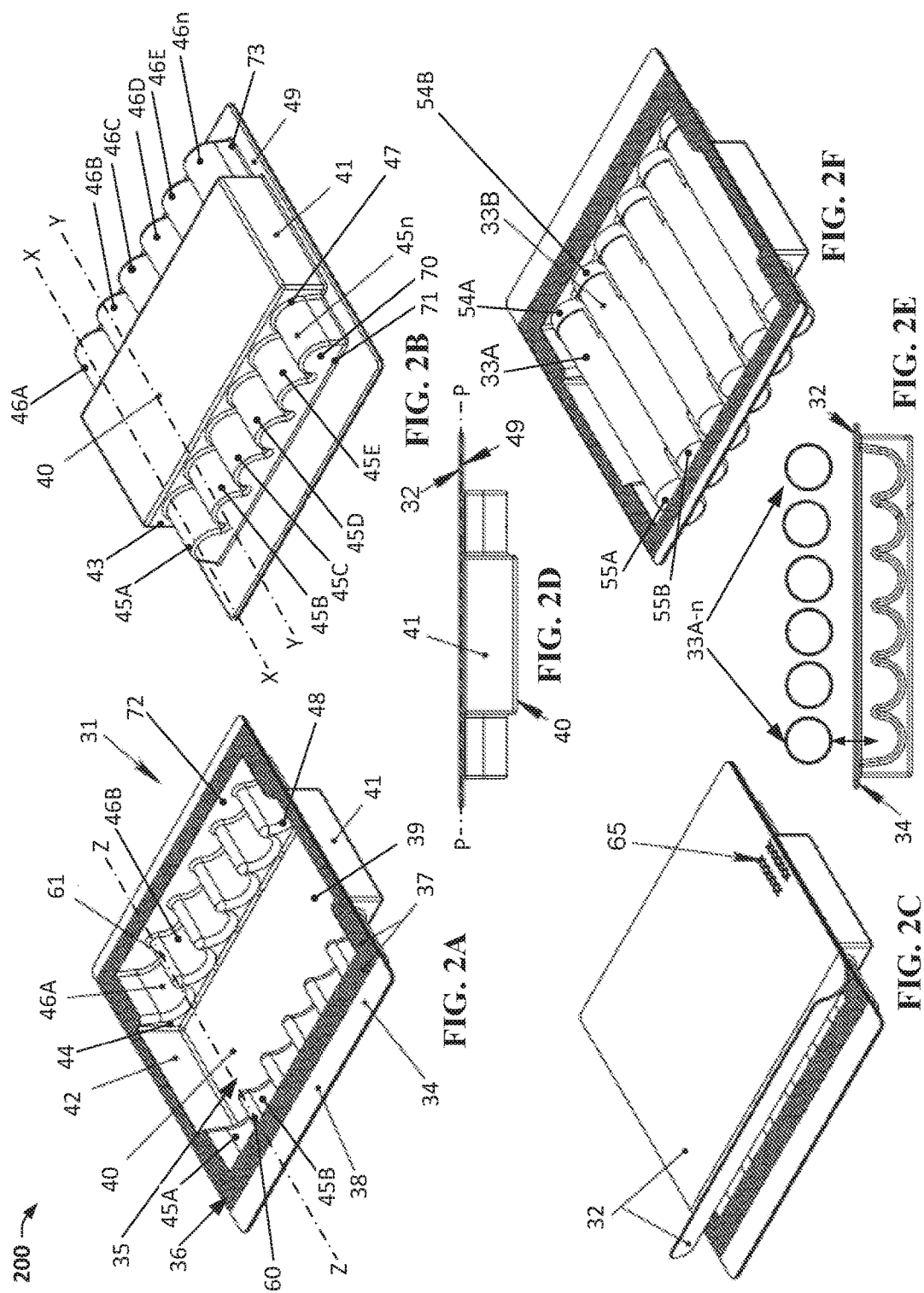

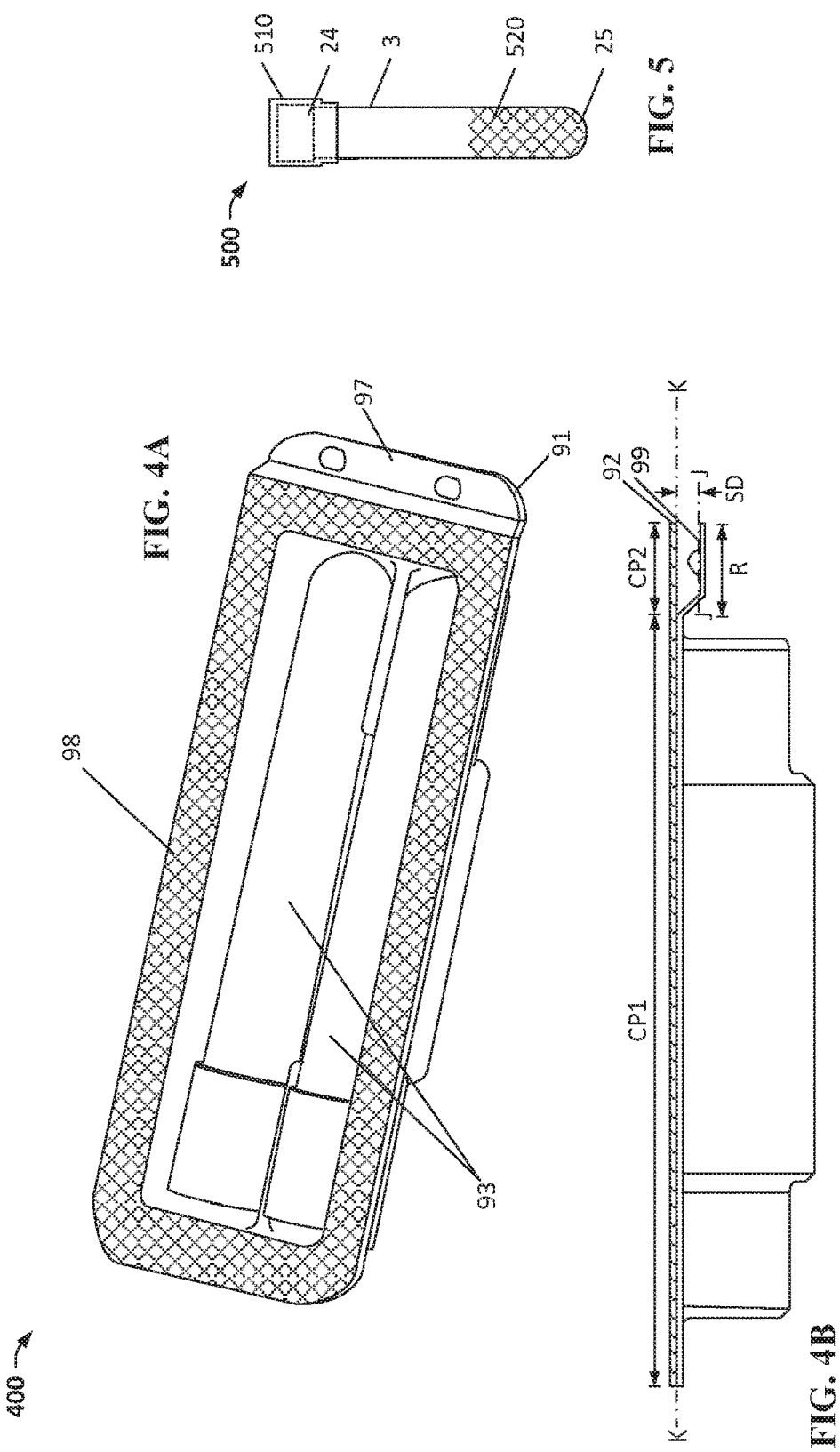

STERILE FLUID COLLECTION TUBE PACKAGE

RELATED APPLICATION

This application claims priority to U.S. Provisional Patent Application No. 62/102,683, filed on Jan. 13, 2015, and entitled "BLOOD COLLECTION TUBES STERI-PACK", the entirety of which is incorporated herein by reference.

BACKGROUND

Collection tubes are commonly utilized in the medical/veterinary fields to enable collection and storage of fluids (e.g., blood, plasma, etc.). However, such tubes can be fragile and care must be taken in order to package the tubes for safe transportation, storage, and sale.

Blood collection tubes are commonly sold in packs of 40 to 100 units. Conventionally, blood collection tubes oftentimes are packaged using an open foam, cardboard, or plastic base (e.g., a tray) with a wrap film cover. Such packaging can be satisfactory in the case of blood collection tubes for medical use, e.g., in a laboratory, medical facility, dental facility, etc. However, when the cover is removed to open the package to enable removal of one or more of the tubes for use with a patient, the remaining unused tubes are subsequently kept in an open environment (e.g., the laboratory environment) for further use with other patients. This open storage enables airborne and cross contamination of the exterior parts of the remaining unused tubes, which can lead to false results, etc.

SUMMARY

The following is a brief summary of subject matter that is described in greater detail herein. This summary is not intended to be limiting as to the scope of the claims.

Described herein are various technologies that relate to sterile transport, storage, and operation of fluid collection tubes. Various embodiments presented herein relate to a sterile fluid collection tube package for storage of one or more fluid collection tubes, wherein the fluid collection tubes can be utilized in the collection and storage of fluids (e.g., blood, plasma, etc.). The sterile fluid collection tube package comprises a tray for location and storage of the one or more fluid collection tubes. The tray comprises a flange surrounding a recessed portion, wherein the recessed portion of the tray comprises one or more non-retentive cavities (compartments). Each cavity is respectively configured to store a respective fluid collection tube in the plurality of fluid collection tubes. In an embodiment, neighboring cavities can be separated by a raised portion (a wall) of the recessed region. A cover can be located on, and adhered to, the flange to cover the recessed portion and any fluid collection tubes located therein. To facilitate removal of the one or more fluid collection tubes from the tray, the cover can be removed (e.g., peeled back) to expose the one or more fluid collection tubes. During removal of the cover, the tray can be inverted such that the one or more fluid collection tubes drop out (e.g., under the force of gravity) for subsequent retrieval and/or usage.

The tray, and recess cavity, can be formed by any suitable process. In an embodiment, the tray can be a thermoformed tray. According to this embodiment, the tray can be thermoformed from sheet stock, e.g., the recessed cavity is thermoformed in the sheet stock. In another embodiment, the tray can be formed by an injection molding process. The tray can be formed from a sterile material. Suitable materials for the tray include a synthetic resin, a sterile foam, polyurethane, polyethylene terephthalate (PET), polyvinyl chloride (PVC), polyester, a combination thereof, etc. The cover can also be formed from a sterile material. The cover material can be at least one of paper, reinforced paper, synthetic reinforced paper, polyethylene terephthalate (PET), polyethylene terephthalate glycol-modified (PET-G), amorphous PET (A-PET), recycled PET (rPET), high impact polystyrene (HIPS), polyvinyl chloride (PVC), polyethylene (PE), high density PE, polypropylene (PP), metal foil, TYVEK, TYVEK 2FS, BARER, TRITON, etc. Further, any suitable bonding process can be utilized to attach the cover to the flange of the tray, e.g., thermo-bonding, adhesive, etc. Where an adhesive is utilized, the adhesive can have a composition to enable the cover to be resealed to the tray after removal of the one or more fluid collection tubes located therein (e.g., for subsequent fluid collection tube storage). The respective materials used for the tray, the cover and the adhesive (if utilized) can be sterile materials, e.g., materials designated for medical usage.

The above presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF THE DRAWINGS

FIGS. 1A-1D illustrate views of an exemplary sterile fluid collection tube package that includes a tray, a cover, and a fluid collection tube.

FIGS. 2A-2F illustrate views of another exemplary sterile fluid collection tube package that includes a tray, a cover, and a plurality of fluid collection tubes

FIGS. 4A-B illustrate views of another exemplary sterile fluid collection tube package.

FIG. 5 illustrates an exemplary fluid collection tube.

DETAILED DESCRIPTION

Figure 3C:
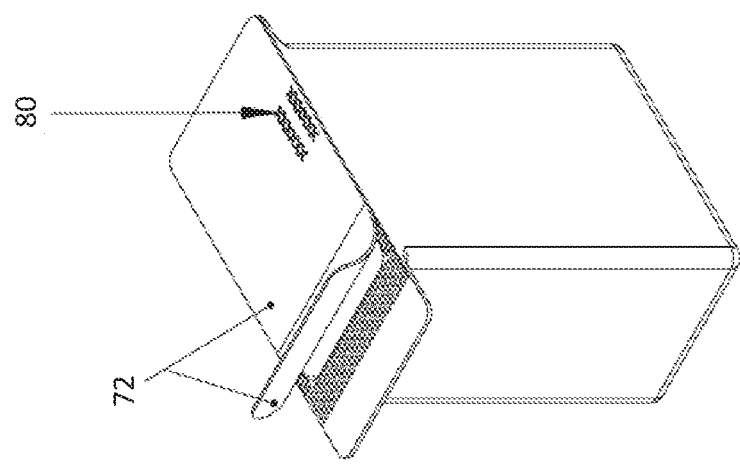
FIGS. 3A-3C illustrate views of another exemplary sterile fluid collection tube package.

Various technologies are presented herein pertaining to sterile transport, storage and operation of fluid collection tubes, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects.

Further, the term "or" is intended to mean an inclusive "or" rather than an exclusive "or". That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. Additionally, as used herein, the term "exemplary" is intended to mean serving as an illustration or example of something, and is not intended to indicate a preference.

Sterile packaging and storage of fluid collection tubes can be important for collection tube usage in operatory rooms as well as in the processing of platelet-rich plasma (PRP), blood concentrates, growth factors, platelet-rich fibrin (PRF), etc. For example, benefits can result from using sterile packaging and storage of fluid collection tubes that are employed when blood is collected from a patient, processed, and brought back to the patient's surgical sites or body. Hence, fluid collection tubes being sterile at time of usage can enhance an ability to obtain valid results and to further mitigate complications related to contamination.

Thus, as set forth herein, it is desired that fluid collection tubes (subsequently referred to herein as tube(s), collection tube(s), fluid collection tube(s), retention tube(s), etc.) are maintained in a sterile atmosphere until use. However, owing to conventional packaging, a plurality of collection tubes are commonly supplied in a single package, such that upon opening the package to retrieve a collection tube, the tubes in the package, including unused tubes, are exposed to the atmosphere (e.g., in the laboratory) which can lead to undesirable conditions such as cross contamination. The various embodiments presented herein enable packing and storage of one or more collection tubes in a sterile configuration to avoid contamination (e.g., cross contamination, airborne contamination, etc.) to minimize false results and provide protection against breakage, with a low inherent cost.

A plurality of embodiments are presented herein, which compared with conventional tube packaging and storage, can have the following benefits. The tubes contained in the packages are not restrictively held, hence the tubes can be easily dispensed from the non-retentive package, e.g., in a sterile environment. In an embodiment, the package can be utilized for single use, e.g., once the sterile package is opened (e.g., cover removed) the tubes contained therein are utilized for a single patient. The tray and cover comprising the package are formed with medical grade materials to validate sterility.

FIGS. 1A-D present various perspective views illustrating a sterile fluid collection tube package 100 configured to store a fluid collection tube 3. FIGS. 1A-1D collectively present a plurality of views of a tray 1, a cover 2 (cover layer), and the fluid collection tube 3, wherein the figures can be read in combination. The fluid collection tube 3 can be a blood collection tube, for example; however, it is contemplated that other types of fluid collection tubes are intended to fall within the scope of the hereto appended claims. Moreover it is to be appreciated that other types of sample tubes can fall within the scope of the claims, e.g., the fluid collection tube 3 can be a sample tube. FIG. 1A is a top view illustrating a flange 4 of the tray 1 and an internal perspective of a cavity 5 formed therein. The flange 4 has an upper surface 6. As shown, the cavity 5 is generally located centrally within the tray 1 with respect to the flange 4, such that the cavity 5 is surrounded by the flange 4. Hence, as shown in FIG. 1A, the flange 4 forms a periphery of (e.g., acts as a boundary to) a central region, wherein the central region defines the cavity 5 surrounded by the flange 4.

As further shown (e.g., FIGS. 1C and 1D), the cover 2 (e.g., a removable film) can be located on the tray 1 wherein a portion of the cover 2 is configured to attach to a portion 7 of the flange 4 such that the cavity 5 is covered and sealed by the cover 2. The flange portion 7 can have a roughened surface to facilitate attachment to the cover 2, wherein attachment of the cover 2 to the tray 1 can be by any suitable technology, e.g., thermo-sealing, adhesive, etc. The roughened surface of the flange portion 7 can be formed by any suitable process, e.g., patterning during the thermoforming process, a patterned injection mold, marking, abrasion, etc. The flange 4 can further have a smooth, non-rough portion 8 (e.g., a non-adhered portion), wherein the smooth portion 8 enables the cover 2 to be removed (e.g., peeled back) from the tray 1 to expose the fluid collection tube 3 stored therein (e.g., as shown in FIG. 1C). The rough portion 7 and the smooth portion 8 can be located on the upper surface 6 of the flange 4.

The cavity 5 can be configured to retain (contain, locate, store) the fluid collection tube 3. The cavity 5 can be configured (e.g., formed) such that it comprises three portions: a central region C, a first end portion D, and a second end portion E, wherein the central region C is located between the first end portion D and the second end portion E. Hence, as further described, the central region C, the first end portion D, and the second end portion E can be formed such that a trough-like cavity 5 is formed that can retain a fluid collection tube 3 located therein, e.g., with or without application of the cover 2. The central region C can comprise a rectangular section 9 having a base wall 10, a first sidewall 11, a second sidewall 12, a third sidewall 13, and a fourth sidewall 14, wherein the first sidewall 11 and second sidewall 12 are opposite, and the third sidewall 13 and the fourth sidewall 14 are opposite (e.g., a three dimensional cuboid, wherein one side forms an opening, such as a trough-like configuration). The base wall 10 is recessed with respect to the upper surface 6 of the flange 4, and the first sidewall 11, the second sidewall 12, the third sidewall 13, and the fourth sidewall 14 join the base wall 10 to the flange 4. The third sidewall 13 is proximally located to the smooth portion 8 of the flange 4, while the fourth sidewall 14 is distally located from the smooth portion 8 of the flange 4 relative to the third sidewall 13.

The first end portion D and second end portion E respectively comprise a first support recess 15 and a second support recess 16. The first support recess 15 and the second support recess 16 are aligned along a first common axis A-A and are respectively located about the rectangular section 9 to form a first compartment comprising the first support recess 15, the rectangular section 9, and the second support recess 16. The first support recess 15 is located at a first junction 17 between the flange 4 and the third sidewall 13, and the second support recess 16 is located at a second junction 18 between the flange 4 and the fourth sidewall 14, as shown in FIG. 1D.

A first interior surface 19 of the first support recess 15 is concave with respect to a plane B-B formed by the upper surface 6 of the flange 4 (orientation of the plane B-B is shown in FIG. 1D), e.g., a radius of curvature of the interior surface 19 has a center located between the interior surface 19 and the plane B-B. Accordingly, the first support recess 15 has a concavo-convex profile, wherein the interior surface 19 is a concave surface and an exterior surface of the first support recess 15 has a convex surface. A second interior surface 20 of the second support recess 16 is concave with respect to the plane B-B formed by the upper surface 6 of the flange 4, e.g., a radius of curvature of the interior surface 20 has a center located between the interior surface 20 and the plane B-B. Accordingly, the second support recess 16 has a concavo-convex profile, wherein the interior surface 20 is a concave surface and an exterior surface of the second support recess 16 has a convex surface. The plane B-B formed by the upper surface 6 of the flange 4 can be considered to be equivalent (e.g., similarly aligned) to a plane formed by the cover 2 when the cover 2 is attached to the tray 1 (as shown in FIG. 1D).

As shown in FIG. 1B, the first support recess 15 terminates with a first end wall 21, wherein the first end wall 21 joins the first support recess 15 with the flange 4, and the first end wall 21 is located at a second end of the first support recess 15 that is opposite to a first end of the first support recess 15 that adjoins to the sidewall 13. As shown in FIG. 1A, the second support recess 16 terminates with a second end wall 22, wherein the second end wall 22 joins the second support recess 16 with the flange 4, and the second end wall 21 is located at a second end of the second support recess 16 that is opposite to a first end of the second support recess 16 that adjoins to the sidewall 14.

As also shown in FIG. 1B, the flange 4 has a lower surface 23, wherein the cavity 5 extends away from the lower surface 23 such that an exterior surface of the base wall 10 is located closer to the lower surface 23 of the flange 4 in comparison to a distance between the exterior surface of the base wall 10 and the upper surface 6 of the flange 4.

The fluid collection tube 3 can comprise of a first end 24 (e.g., a cap, a stopper located in an open end of the tube 3) and a second end 25 (e.g., a closed end of the tube 3), or vice versa. The tube 3 can be located in the cavity 5, wherein the first end 24 of the tube 3 can be located in the first support recess 15 and the second end 25 of the tube 3 can be located in the second support recess 16.

Hence, as shown in FIG. 1D, the tube 3 (denoted by the dashed, hidden detail line) is located in the cavity 5 formed by the central rectangular section 9 in combination with the first support recess 15 and the second support recess 16. The tube 3 is sealed in the cavity 5 by the cover 2 attached to the upper surface 6 of the flange 4 to cover over the cavity 5. The tube 3 has a length and a width, wherein the cavity 5 comprising the first support recess 15, the second support recess 16, and the central rectangular section 9 has a length having a dimension longer than the length of the tube, and further, the first support recess 15, the second support recess 16, and the central rectangular section 9 have a width (diameter) greater than the width of the tube 3. As shown in FIG. 1D, with the tube 3 located in the cavity 5 of the tray 1, and the cover 2 located over the cavity 5 and attached to the flange portion 7, the tube 3 is retained in a sterile atmosphere created by enclosing the tube 3 in a volume of gas (e.g., air, sterilized air, or other gas), wherein the volume of gas is defined by the volume created by the cavity 5 and the cover 2 located thereon. In an embodiment, the sterile fluid collection tube package 100, including the tray 1, the cover 2, and the fluid collection tube(s) 3 can be sterilized, e.g., by irradiating with gamma radiation, or other suitable sterilizing technique. Such sterilization can cause the volume of gas in the cavity 5 to also be sterilized.

The tray 1, and cavity 5 formed therein, can be formed by any suitable process. In an embodiment, the tray 1 can be thermoformed from sheet stock, e.g., the recessed cavity 5 is thermoformed in the sheet stock, wherein the non-deformed region of the sheet stock can form the flange 4. In another embodiment, the tray 1 can be formed by an injection molding process. The tray 1 can be formed from any suitable material, wherein the material is a sterile material (e.g., is rated as suitable for medically sterile applications, is rated as suitable for a medical application, etc.). The material for the tray 1 can, in a non-limiting list, include any of a synthetic resin, a sterile foam, a thermoplastic, a polymer, polyurethane, polyethylene terephthalate (PET), polyvinyl chloride (PVC), polyester, etc. The tray 1 can be formed from material that is resiliently deformable, to minimize impact on the one or more collection tubes 3 located therein. The tray 1 can be formed from sheet material having any desired thickness (e.g., as based upon a desired wall thickness and/or dimension of any of the thermoformed base wall 10, the first sidewall 11, the second sidewall 12, the third sidewall 13, and/or the fourth sidewall 14). In an embodiment the sheet material can have a minimum thickness of about 0.4 mm (e.g., about 0.015"). In another embodiment, the sheet material can have a thickness of about 0.5 mm (e.g., about 0.02"). In another embodiment the sheet material can have a thickness in the range of about 0.4 mm to about 0.8 mm (e.g., about 0.015" to about 0.0315"). In a further embodiment, the sheet material can have a thickness of greater than about 0.8 mm (e.g., about 0.0315"). In another embodiment, the sheet material can have a minimum thickness of 0.4 mm and greater than 0.8 mm (e.g., about 0.015" to ≥0.0315"). The thicknesses presented here can also be applied to a wall thickness(es) of a tray 1 that has been formed by injection molding.

The cover 2 can comprise any suitable material, wherein the material is sterile (e.g., is rated as suitable for medically sterile applications). The material for the cover 2 can, in a non-limiting list, include at least one of paper, reinforced paper, synthetic reinforced paper, polyethylene terephthalate (PET), polyethylene terephthalate glycol-modified (PET-G), amorphous PET (A-PET), recycled PET (rPET), high impact polystyrene (HIPS), polyvinyl chloride (PVC), polyethylene (PE), high density PE, polypropylene (PP), metal foil, TYVEK, TYVEK 2FS, BAREX, TRITON, etc. Further, any suitable bonding process can be utilized to attach the cover 2 to the flange 4 of the tray, e.g., thermo-bonding, adhesive, etc. In the event of an adhesive being utilized, the adhesive (not shown) can have a composition to enable the cover 2 to be resealed to the tray 1 after removal of the one or more collection tubes 3 located therein. The respective thicknesses of the tray 1 and the cover 2 can be of any desired value. The cover 2 can be formed from sheet material having any desired thickness to facilitate sealing of the cavity 5, and the tube(s) 3 located therein. In an embodiment the sheet material can have a thickness of about 0.0028-0.0092" mils (about 70-230 microns). In another embodiment, the sheet material can have an average thickness of about 0.00598" mils (about 152 microns).

As shown in FIG. 1C, the cover 2 can include a data region, e.g., a label 26, wherein the label 26 can provide information such as branding (e.g., manufacturer of the tube 3, a type of tube 3, manufacturer of the package 100, manufacturer of the tray 1, manufacturer of the cover 2, etc.), technical information, traceability information, etc. The label 26 can be printed on, or attached to, the cover 2, wherein the label 26 can be of any suitable form, e.g., alphanumeric information, a barcode, a hologram, etc.

As previously mentioned, a tray can be configured to store more than one collection tube. FIGS. 2A-2F present various perspective views illustrating a sterile fluid collection tube package 200 configured to store two or more fluid collection tubes. In the example depicted in FIGS. 2A-2F, the sterile fluid collection tube package 200 stores six fluid collection tubes; however, it is contemplated that substantially any number of fluid collection tubes are intended to fall within the scope of the hereto appended claims.

FIGS. 2A-2F collectively present a plurality of views of a tray 31, a cover 32, and a plurality of fluid collection tubes 33A-n (where n is a positive integer), wherein the figures can be read in combination. FIG. 2A is atop view illustrating a flange 34 of the tray 31 and an internal perspective of a cavity 35 formed therein. The flange 34 has an upper surface 36. As shown, the cavity 35 is generally located centrally within the tray 31, such that the cavity 35 is surrounded by the flange 34.

The various components and features presented in FIGS. 2A-2F are similar to respective components and features described in FIGS. 1A-1D. For example, the tray 31 can be formed using the same processes and materials as tray 1, the cover 32 can be formed using the same processes and materials as cover 2, and the fluid collection tubes 33 can be formed from the same processes and materials as collection tube 3.

As shown in FIG. 2C, and as previously described with reference to FIGS. 1A-1D, the cover 32 can be located on the tray 31 wherein a portion of the cover 32 is configured to attach to a portion 37 of the flange 34 such that the cavity 35 is covered and sealed by the cover 32. The flange portion 37 can have a roughened surface to facilitate attachment to the cover 32, wherein attachment can be via any suitable operation, e.g., the cover 32 is thermo-sealed to the tray 31. The flange 34 can further have a smooth, non-rough portion 38 (e.g., non-adhered portion), wherein the smooth portion 38 enables the cover 32 to be removed from the tray 31 to expose collection tubes 33A-n stored therein. The rough portion 37 and the smooth portion 38 can be located on the upper surface 36 of the flange 34.

As previously described with reference to FIGS. 1A-1D, the cavity 5 can be formed with a single compartment comprising the rectangular section 9 located between the first support recess 15 and the second support recess 16. As shown in FIGS. 2A-2F, to facilitate storage of a plurality of collection tubes 33A-n, the cavity 35 can be formed comprising a plurality of compartments. The cavity 35 can be formed with a central rectangular section 39 located between a first plurality of first support recesses 45A-n and a second plurality of second support recesses 46A-n, wherein the number n of first support recesses 45 and the number n of second support recesses 46 is equivalent to the number n of collection tubes 33A-n to be stored therein. The cavity 35 comprising a plurality of compartments can be considered to be formed from a plurality of co-joined single compartments, wherein a single compartment forms the cavity 5 of FIG. 1A.

The rectangular section 39 has a base wall 40, a first sidewall 41, a second sidewall 42, a third sidewall 43, and a fourth sidewall 44, wherein the first sidewall 41 and second sidewall 42 are opposite, and the third sidewall 43 and the fourth sidewall 44 are opposite (e.g., the rectangular section 39 has a trough-like configuration). The base wall 40 is recessed with respect to the upper surface 36 of the flange 34, and the first sidewall 41, the second sidewall 42, the third sidewall 43, and the fourth sidewall 44 join the base wall 40 to the flange 34. The third sidewall 43 is proximally located to the smooth portion 38 of the flange 34, while the fourth sidewall 44 is distally located from the smooth portion 38 of the flange 34 relative to the third sidewall 43.

As shown in FIG. 2B, respective pairs of first support recesses and second support recesses are aligned along a common axis. For example, a first pair of support recesses comprising a first support recess 45A and a second support recess 46A are aligned along a common axis X-X, a second pair of support recesses comprising a third support recess 45B and a fourth support recess 46B are aligned along a common axis Y-Y, etc. Each respective pair of first support recesses and second support recesses, in conjunction with a respective portion of the rectangular section 39 located between each respective pair of first support recesses and second support recesses, form a compartment (a channel). Hence, the first support recess 45A and the second support recess 46A, in conjunction with a first portion of the rectangular section 39 form a first compartment to store a first a separating wall 60 separates the first support recess 45A and the third support recess 45B collection tube 33A, the third support recess 45B and the fourth support recess 46B, in conjunction with a second portion of the rectangular section 39 form a second compartment to store a second collection tube 33B, the $n^{th}$ support recess $45n$ and the $n^{th}$+1 support recess $46n$, in conjunction with a second portion of the rectangular section 39 form an $n^{th}$ compartment to store a $n^{th}$ collection tube $33n$.

The respective interior surfaces of the support recesses 45A-$45n$ and 46A-$46n$ are concave with respect to a plane P-P formed by the upper surface 36 of the flange 34 (orientation of the plane P-P is shown in FIG. 2D), as previously described with regard to support recesses 15 and 16, accordingly the support recesses 45A-n and 46A-n have a concavo-convex profile. Separating walls (ridges) are located between adjacent compartments, e.g., as shown in FIG. 2A, a first separating wall 60 separates the first support recess 45A and the third support recess 45B, a second separating wall 61 separates the second support recess 46A and the fourth support recess 46B. The first separating wall 60 and the second separating wall 61 are aligned along a common axis Z-Z, wherein the axis Z-Z is parallel to the axis X-X and the axis Y-Y. With respect to the support recesses 45A-$45n$ and 46A-$46n$ having a concavo-convex profile with regard to plane P-P, in an embodiment, the separating walls 60 and 61 have a concavo-convex profile such that the separating wall in conjunction with the walls of the adjacent support recesses has a serpentine profile. In another embodiment, the separating walls 60 and 61 have a flat profile.

Further, as previously described, a first end of each respective support recess forms a junction with a respective sidewall that it adjoins (e.g., per the configuration presented in FIGS. 1A-1D, a first end of the first support recess 15 is located at a first junction 17 between the flange 4 and the third sidewall 13, and the first end of the second support recess 16 is located at a second junction 18 between the flange 4 and the fourth sidewall 14.). Hence, a first end of the first support recess $45n$ is located at a first junction 47 between the flange 34 and the third sidewall 43 (per FIG. 2B), and a first end of the second support recess $46n$ is located at a second junction 48 between the flange 34 and the fourth sidewall 44 (per FIG. 2A).

As shown in FIG. 2B, the flange 34 has a lower surface 49, wherein the cavity 35 extends away from the lower surface 49 such that an exterior surface of the base wall 40 is located closer to the lower surface 49 of the flange 34 in comparison to a distance between the exterior surface of the base wall 40 and the upper surface 36 of the flange 34. Furthermore, as shown in FIGS. 2A and 2B, each support recess terminates with an end wall, wherein the end wall connects a second end of a support recess with the flange 34. A first end wall 70 connects the second end of each respective first support recess 45A-n to the flange 34, wherein the first end wall 70 forms a first junction 71 with the underside surface 49 of the flange 34. A second end wall 72 connects the second end of each respective second support recess 46A-n to the flange 34, wherein the first end wall 72 forms a first junction 73 with the underside surface 49 of the flange 34.

The tubes 33A-n can respectively comprise of first end (e.g., a cap, a stopper located in an open end of the tube) and a second end (e.g., a closed end of the tube), or vice versa. Per FIG. 2F, a plurality of tubes 33A-n are located in the tray 31, wherein tube 33A has a first end 54A and a second end 55A. The tubes 33A-n can be located in the cavity 35, wherein the tube 33A is located in the first compartment formed between the first support recess 45A and the second support recess 46A, the tube 33B is located in the second compartment formed between the third support recess 45B and the fourth support recess 46B, etc.

FIG. 2F illustrates a plurality of tubes 33A-n located in the tray 31, tube 33A is located in the support recesses 54A and 55A, tube 33B is located in the support recesses 54B and 55B, wherein the tubes are separated by both the respective support recesses and the respective separating walls 60 and 61. As shown in FIG. 2C, the tubes 33A-n are sealed in the cavity 35 by the cover 32 attached to the upper surface 36 of the flange 34 to cover over the cavity 35.

As further shown in FIG. 2F, the cover 32 can include a data region, e.g., a label 65, wherein the label 65 can be of the form, and include information, as previously described for the label 26.

Figure 3B:
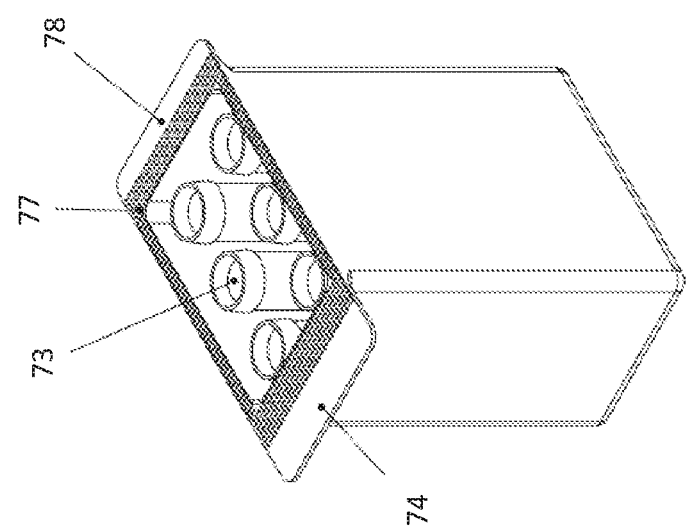
Figure 3A:
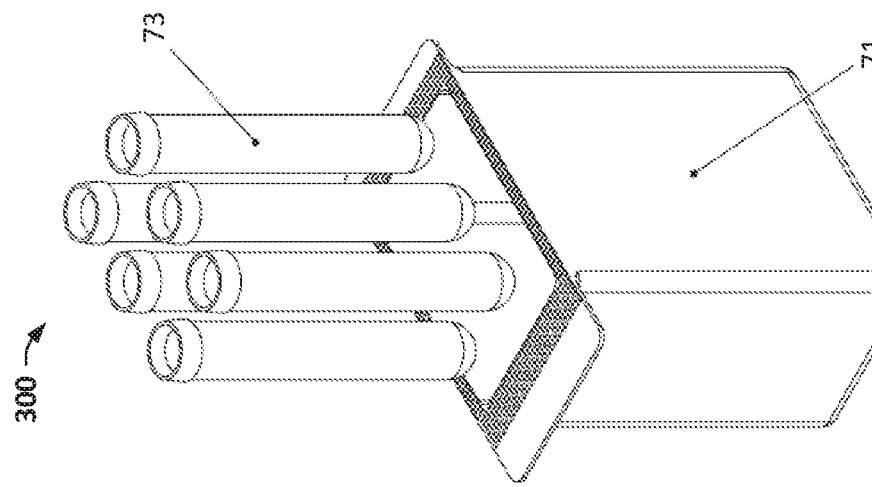

FIGS. 3A-C are a perspective views of another exemplary sterile collection tube package 300. As shown, the previously described trays (e.g., tray 1 and tray 31) have been configured as a box-like tray 71, having exterior flat rectangular side walls and a flat exterior base with interior round openings so that the tubes will be held in a vertical position. A cover 72 is shown, and further, a plurality of tubes 73. It is to be appreciated that while six tubes 73 are illustrated, the tray 71 can be formed for a required n number of tubes 73. Accordingly, a number of round openings will vary for the box tray 71 designed to hold different number of collection tubes 73, for example, the box-like tray 71 designed to hold eight collection tubes 73 will have eight round openings (not illustrated). FIG. 3A illustrates six collection tubes 73 prior to being placed inside the box tray 71. FIG. 3B illustrates the collection tubes 73 placed inside the box. An upper flange 74 of the box tray 73 is a flat surface rectangular shape (e.g., similar to flange 4 and flange 34), configured with an adhesive marks portion 77 to enable sealing engagement with the cover 72 and a smooth portion 74 without adhesive marking to enable easy peel removal of the cover 72 from the flange 74. FIG. 3C illustrates the cover 72 attached to the flange 74, and further a label 80 incorporated into the cover 72. The box tray 71 can be fabricated by the same process as tray 1, and further the box tray 71 can be formed from the same materials as tray 1. The cover 72 can be fabricated by the same process as cover 2, and further the cover 72 can be formed from the same materials as cover 2. The label 80 can be formed and function the same as the previously described label 26.

FIGS. 4A and 4B illustrates an alternative embodiment for the flange that surrounds the central cavity region. As shown in FIGS. 1-3, the respective smooth portions of the flange (e.g., respective regions 8, 38, 78) are illustrated as being in the same plane as the roughened regions (e.g., regions 7, 37, 77) of the flange at which the respective cover (e.g., cover 2, 32, 72) is attached (e.g., by thermo-bonding). For example, the flange smooth portions illustrated in FIGS. 1-3 are aligned in the same plane (e.g., plane B-B, plane P-P) as the respective roughened portions. FIGS. 4A and 4B illustrate a tray 91, to which a cover 92 can be attached, to enable sterile storage of a plurality of tubes 93 therein. While only two tubes 93 are illustrated, the tray 91 can be configured to store 1-n tubes, as previously described. As shown, an interface at which the cover 92 and the roughened portion 98 of the flange 91 are attached can be aligned along the plane K-K. Further, an end portion 97 of the flange 91 can be offset from plane K-K, wherein the end portion 97 is aligned along a plane J-J, wherein planes K-K and J-J have different alignments and/or orientations. Accordingly, while a first portion CP1 of the cover 2 is attached to the roughened portion 98, a second portion CP2 of the cover 2 is not attached to the offset flange end portion 97, such that an upper surface 99 of the end portion 97 on the plane J-J is located at a separation distance SD from the plane K-K.

While not illustrated, it is to be appreciated that the one or more tray configurations presented herein (e.g., tray 1, tray 31, tray 71) can be formed without one or more sidewalls being formed (e.g., any of the sidewall 11, the sidewall 12, the sidewall 13, the sidewall 14, base 10, the sidewall 41, the sidewall 42, the sidewall 43, the sidewall 44, the base 40, etc.), wherein the tray (with or without a cover) can be sealed inside a double or triple medical grade sealed bag.

FIG. 5 illustrates a configuration 500 with a collection tube that has been sealed with a cap and a hood. The collection tube 3 has a closed end 25 and an open end that is sealed with a cap 24 (as previously described). A hood 510 has been placed over the cap 24 and a portion of a length of the tube 3, wherein the hood 510 is configured to supplement the cap 24 in sealing a sample 520 in the tube 3. The hood 510 can be formed from a flexible, elastic material formulated to prevent leakage of air into and/or out of the tube 3, wherein such air leakage could contaminate the sample 520. The hood 510 can also be utilized with a tube 3 and cap 24 that does not have a sample 520 placed therein. The dimensioning of the cavity 5 (e.g., the width of the first recess 15) can be configured to accommodate a tube 3 sealed with a cap 24 and the hood 510.

Various examples are now set forth.

Example 1

A sterile fluid collection tube package, comprising: a fluid collection tube having first end and a second end; a thermoformed tray formed from a first sterile material, the thermoformed tray comprising a flange having an upper surface, and a central region, wherein the central region defines a cavity surrounded by the flange, the cavity comprising: a recessed portion comprising a rectangular section having a base wall, a first sidewall, a second sidewall, a third sidewall, and a fourth sidewall, the first sidewall and second sidewall are opposite, and the third sidewall and the fourth sidewall are opposite, the base wall is recessed with respect to the upper surface of the flange, and the first sidewall, the second sidewall, the third sidewall, and the fourth sidewall join the base wall to the flange; a first support recess and a second support recess, the first support recess and the second support recess are aligned along a first common axis and are respectively located about the recessed portion to form a first compartment, wherein the first support recess is located at a first junction between the flange and the third sidewall, and the second support recess is located at a second junction between the flange and the fourth sidewall, a first interior surface of the first support recess is convex with respect to a plane formed by the upper surface of the flange and a second interior surface of the second support recess is convex with respect to the plane formed by the upper surface of the flange, wherein the fluid collection tube is located in the cavity, the first end of the fluid collection tube is located in the first support recess and the second end of the fluid collection tube is located in the second support recess; and a cover formed from a second sterile material, the cover is attached to the upper surface of the flange, wherein the cover is sized to cover an entirety of the cavity and the fluid collection tube located therein.

Example 2

The sterile fluid collection tube package according to Example 1, wherein the first sterile material is one of a synthetic resin, a sterile foam, polyurethane, polyethylene terephthalate (PET), polyvinyl chloride (PVC), or polyester.

Example 3

The sterile fluid collection tube package according to any of Examples 1-2, wherein the second sterile material comprises at least one of paper, reinforced paper, synthetic reinforced paper, polyethylene terephthalate (PET), polyethylene terephthalate glycol-modified (PET-G), amorphous PET (A-PET), recycled PET (rPET), high impact polystyrene (HIPS), polyvinyl chloride (PVC), polyethylene (PE), high density PE, polypropylene (PP), metal foil, TYVEK, TYVEK 2FS, BAREX, or TRITON.

Example 4

The sterile fluid collection tube package according to any of Examples 1-3, further comprising a releasable adhesive, wherein the cover is attached to the upper surface of the flange by the releasable adhesive, and the releasable adhesive facilitates removal of the cover from the thermoformed tray.

Example 5

The sterile fluid collection tube package according to any of Examples 1-4, wherein: the first support recess opens into the recessed portion, the first support recess further comprising a first end wall, a first edge of the first end wall adjoins the flange, and a second edge of the first end wall follows a convex profile of the first interior surface of the first support recess; and the second support recess opens into the recessed portion, the second support recess further comprising a second end wall, a third edge of the second end wall adjoins the flange, and a fourth edge of the second wall follows a convex profile of the second interior surface of the second support recess.

Example 6

The sterile fluid collection tube package according to any of Examples 1-5, wherein the thermoformed tray is formed from a sheet of the sterile thermoplastic, the sheet having a thickness in a range between 4 mm and 8 mm.

Example 7

The sterile fluid collection tube package according to any of Examples 1-6, wherein the fluid collection tube has a length and a width, wherein the first support recess, the second support recess, and a first portion of the recessed portion are dimensioned such that the fluid collection tube is located in a compartment formed by the first support recess, the second support recess, and the first portion of the recessed portion.

Example 8

The sterile fluid collection tube package according to any of Examples 1-7, further comprising a third support recess and a fourth support recess, the third support recess and the fourth support recess are aligned along a second common axis and are respectively located about the recessed portion to form a second compartment, the first common axis and the second common axis are substantially parallel, wherein the third support recess is located at a third junction between the flange and the third sidewall, and the fourth support recess is located at a fourth junction between the flange and the fourth sidewall, a third interior surface of the third support recess is convex with respect to the plane formed by the upper surface of the flange and a fourth interior surface of the fourth support recess is convex with respect to the plane formed by the upper surface of the flange, wherein a second fluid collection tube is located in the second compartment.

Example 9

The sterile fluid collection tube package according to any of Examples 1-8, wherein the fluid collection tube is a blood collection tube.

Example 10

A package configured to retain at least one sample tube, the package comprising: a tray comprising a flange surrounding a recessed portion, wherein the tray is formed from a sterile thermoplastic, the recessed portion of the tray comprising: a rectangular section having a base wall, a first sidewall, a second sidewall, a third sidewall, and a fourth sidewall, the first sidewall and second sidewall are opposite, and the third sidewall and the fourth sidewall are opposite, and the first sidewall, the second sidewall, the third sidewall, and the fourth sidewall join the base wall to the flange; and a first compartment, wherein the first compartment is configured to receive a first sample tube, the first compartment comprising a first support recess and a second support recess, the first support recess has a first length and the second support recess has a second length, wherein the first length and the second length are aligned along a first common axis and are respectively located about the rectangular section, wherein: a fifth sidewall extending along the first length of the first support recess is concavo-convex with respect to a plane formed by the flange, a first end of the first support recess is located at a first junction between the flange and the third sidewall and opens into the rectangular section, a second end of the first support recess connects the fifth sidewall to the flange; and a sixth sidewall extending along the second length of the second support recess is concavo-convex with respect to the plane formed by the flange, a third end of the second support recess is located at a second junction between the flange and the fourth sidewall and opens into the rectangular section, a fourth end of the second support recess connects the sixth sidewall to the flange.

Example 11

The package according to Example 10, wherein the sterile thermoplastic is one of a synthetic resin, a sterile foam, a polyurethane film, polyethylene terephthalate (PET), polyvinyl chloride (PVC), or polyester.

Example 12

The package according to any of Examples 10 and 11, wherein the tray is formed from a sheet of the sterile thermoplastic, the sheet having a thickness in a range between 4 mm and 8 mm.

Example 13

The package according to any of Examples 10-12, further comprising a cover formed from a sterile material, the cover is attached to an upper surface of the flange, wherein the cover is sized to cover an entirety of the recessed portion of the tray.

Example 14

The package according to any of Examples 10-13, wherein the sterile material comprises at least one of paper, a reinforced paper, a synthetic reinforced paper, polyethylene terephthalate (PET), polyethylene terephthalate glycol-modified (PET-G), amorphous PET (A-PET), recycled PET (rPET), high impact polystyrene (HIPS), polyvinyl chloride (PVC), polyethylene (PE), high density PE, polypropylene (PP), metal foil, TYVEK, TYVEK 2FS, BAREX, or TRITON.

Example 15

The package according to any of Examples 10-14, further comprising a releasable adhesive, wherein the cover is attached to the upper surface of the flange by the releasable adhesive, and the releasable adhesive facilitates removal of the cover from the tray.

Example 16

The package according to any of Examples 10-15, further comprising the first sample tube, wherein the first compartment is configured to store the first sample tube, dimensioning of the first compartment is such that the first sample tube can be located within the first compartment.

Example 17

The package according to any of Examples 10-16, wherein the sample tube is a blood collection tube.

Example 18

The package according to any of Examples 10-17, wherein the tray is formed by injection molding the sterile thermoplastic.

Example 19

The package according to any of Examples 10-18, further comprising a label, wherein the label comprises at least one of brand information, technical information, or traceability information.

Example 20

A package configured to retain a fluid collection tube, the package comprising: a means for storing the fluid collection tube in a sterile environment, and a means for covering the fluid collection tube in the sterile environment.

What has been described above includes examples of one or more embodiments. It is, of course, not possible to describe every conceivable modification and alteration of the above structures or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A sterile fluid collection tube package, comprising:
    a fluid collection tube having first end and a second end;
    a thermoformed tray formed from a first sterile material, the thermoformed tray comprising a flange having an upper surface, and a central region, wherein the central region defines a cavity surrounded by the flange, the cavity comprising:
        a recessed portion comprising a rectangular section having a base wall, a first sidewall, a second sidewall, a third sidewall, and a fourth sidewall, the first sidewall and second sidewall are opposite, and the third sidewall and the fourth sidewall are opposite, the base wall is recessed with respect to the upper surface of the flange, and the first sidewall, the second sidewall, the third sidewall, and the fourth sidewall join the base wall to the flange;
        a first support recess and a second support recess, the first support recess and the second support recess are aligned along a first common axis and are respectively located about the recessed portion to form a first compartment, wherein the first support recess is located at a first junction between the flange and the third sidewall, and the second support recess is located at a second junction between the flange and the fourth sidewall, a first interior surface of the first support recess is convex with respect to a plane formed by the upper surface of the flange and a second interior surface of the second support recess is convex with respect to the plane formed by the upper surface of the flange, wherein the fluid collection tube is located in the cavity, the first end of the fluid collection tube is located in the first support recess and the second end of the fluid collection tube is located in the second support recess; and
    a cover formed from a second sterile material, the cover is attached to the upper surface of the flange, wherein the cover is sized to cover an entirety of the cavity and the fluid collection tube located therein.

2. The sterile fluid collection tube package of claim 1, wherein the first sterile material is one of a synthetic resin, a sterile foam, polyurethane, polyethylene terephthalate (PET), polyvinyl chloride (PVC), or polyester.

3. The sterile fluid collection tube package of claim 1, wherein the second sterile material comprises at least one of paper, reinforced paper, synthetic reinforced paper, polyethylene terephthalate (PET), polyethylene terephthalate glycol-modified (PET-G), amorphous PET (A-PET), recycled PET (rPET), high impact polystyrene (HIPS), polyvinyl chloride (PVC), polyethylene (PE), high density PE, polypropylene (PP), metal foil, TYVEK, TYVEK 2FS, BAREX, or TRITON.

4. The sterile fluid collection tube package of claim 1, further comprising a releasable adhesive, wherein the cover is attached to the upper surface of the flange by the releasable adhesive, and the releasable adhesive facilitates removal of the cover from the thermoformed tray.

5. The sterile fluid collection tube package of claim 1, wherein:
the first support recess opens into the recessed portion, the first support recess further comprising a first end wall, a first edge of the first end wall adjoins the flange, and a second edge of the first end wall follows a convex profile of the first interior surface of the first support recess; and
the second support recess opens into the recessed portion, the second support recess further comprising a second end wall, a third edge of the second end wall adjoins the flange, and a fourth edge of the second wall follows a convex profile of the second interior surface of the second support recess.

6. The sterile fluid collection tube package of claim 1, wherein the thermoformed tray is formed from a sheet of the sterile thermoplastic, the sheet having a thickness in a range between 4 mm and 8 mm.

7. The sterile fluid collection tube package of claim 1, wherein the fluid collection tube has a length and a width, wherein the first support recess, the second support recess, and a first portion of the recessed portion are dimensioned such that the fluid collection tube is located in a compartment formed by the first support recess, the second support recess, and the first portion of the recessed portion.

8. The sterile fluid collection tube package of claim 1, further comprising a third support recess and a fourth support recess, the third support recess and the fourth support recess are aligned along a second common axis and are respectively located about the recessed portion to form a second compartment, the first common axis and the second common axis are substantially parallel, wherein the third support recess is located at a third junction between the flange and the third sidewall, and the fourth support recess is located at a fourth junction between the flange and the fourth sidewall, a third interior surface of the third support recess is convex with respect to the plane formed by the upper surface of the flange and a fourth interior surface of the fourth support recess is convex with respect to the plane formed by the upper surface of the flange, wherein a second fluid collection tube is located in the second compartment.

9. The sterile fluid collection tube package of claim 1, wherein the fluid collection tube is a blood collection tube.

10. A package comprising:
at least one blood collection tube; and
a tray comprising a flange surrounding a recessed portion, wherein the tray is formed from a sterile thermoplastic, the recessed portion of the tray comprising:
a rectangular section having a base wall, a first sidewall, a second sidewall, a third sidewall, and a fourth sidewall, the first sidewall and second sidewall are opposite, and the third sidewall and the fourth sidewall are opposite, and the first sidewall, the second sidewall, the third sidewall, and the fourth sidewall join the base wall to the flange; and
a first compartment, wherein the first compartment is configured to receive a first blood collection tube such that the first blood collection tube can be located within the first compartment, the first compartment comprising a first support recess and a second support recess, the first support recess has a first length and the second support recess has a second length, wherein the first length and the second length are aligned along a first common axis and are respectively located about the rectangular section, wherein:
a fifth sidewall extending along the first length of the first support recess is concavo-convex with respect to a plane formed by the flange, a first end of the first support recess is located at a first junction between the flange and the third sidewall and opens into the rectangular section, a second end of the first support recess connects the fifth sidewall to the flange, and edges of the fifth sidewall extending along the first length of the first support recess adjoin the flange; and
a sixth sidewall extending along the second length of the second support recess is concavo-convex with respect to the plane formed by the flange, a third end of the second support recess is located at a second junction between the flange and the fourth sidewall and opens into the rectangular section, a fourth end of the second support recess connects the sixth sidewall to the flange, and edges of the sixth sidewall extending along the second length of the second support recess adjoin the flange.

11. The package of claim 10, wherein the sterile thermoplastic is one of a synthetic resin, a sterile foam, a polyurethane film, polyethylene terephthalate (PET), polyvinyl chloride (PVC), or polyester.

12. The package of claim 10, wherein the tray is formed from a sheet of the sterile thermoplastic, the sheet having a thickness in a range between 4 mm and 8 mm.

13. The package of claim 10, further comprising a cover formed from a sterile material, the cover is attached to an upper surface of the flange, wherein the cover is sized to cover an entirety of the recessed portion of the tray.

14. The package of claim 13, wherein the sterile material comprises at least one of paper, a reinforced paper, a synthetic reinforced paper, polyethylene terephthalate (PET), polyethylene terephthalate glycol-modified (PET-G), amorphous PET (A-PET), recycled PET (rPET), high impact polystyrene (HIPS), polyvinyl chloride (PVC), polyethylene (PE), high density PE, polypropylene (PP), metal foil, TYVEK, TYVEK 2FS, BAREX, or TRITON.

15. The package of claim 13, further comprising a releasable adhesive, wherein the cover is attached to the upper surface of the flange by the releasable adhesive, and the releasable adhesive facilitates removal of the cover from the tray.

16. The package of claim 10, wherein the tray is formed by injection molding the sterile thermoplastic.

17. The package of claim 10, further comprising a label, wherein the label comprises at least one of brand information, technical information, or traceability information.

* * * * *